(12) United States Patent
Chiba et al.

(10) Patent No.: US 11,084,020 B2
(45) Date of Patent: Aug. 10, 2021

(54) WATER-ABSORBENT RESIN AND ABSORBENT ARTICLE

(71) Applicant: SUMITOMO SEIKA CHEMICALS CO., LTD., Hyogo (JP)

(72) Inventors: Mikito Chiba, Himeji (JP); Yuichi Onoda, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 0 days.

(21) Appl. No.: 16/489,854

(22) PCT Filed: Mar. 2, 2018

(86) PCT No.: PCT/JP2018/007959
§ 371 (c)(1),
(2) Date: Aug. 29, 2019

(87) PCT Pub. No.: WO2018/159800
PCT Pub. Date: Sep. 7, 2018

(65) Prior Publication Data
US 2020/0001270 A1    Jan. 2, 2020

(30) Foreign Application Priority Data
Mar. 2, 2017 (JP) .............................. JP2017-038979

(51) Int. Cl.
*B01J 20/28* (2006.01)
*B01J 20/26* (2006.01)
*C08F 20/06* (2006.01)
*C08G 59/42* (2006.01)

(52) U.S. Cl.
CPC ............... *B01J 20/28* (2013.01); *B01J 20/26* (2013.01); *C08F 20/06* (2013.01); *C08G 59/42* (2013.01)

(58) Field of Classification Search
CPC ........... B01J 20/28; B01J 20/26; C08F 20/06; C08G 59/42

USPC ........................................................ 502/402
See application file for complete search history.

(56) References Cited

U.S. PATENT DOCUMENTS

| | | | |
|---|---|---|---|
| 5,180,798 | A | 1/1993 | Nakamura et al. |
| 2003/0181115 | A1 | 9/2003 | Nagasuna et al. |
| 2011/0313113 | A1 | 12/2011 | Sakamoto et al. |
| 2016/0367717 | A1 | 12/2016 | Hinayama et al. |
| 2017/0107313 | A1 | 4/2017 | Murakami et al. |
| 2017/0203279 | A1 | 7/2017 | Murakami et al. |
| 2018/0001300 | A1 | 1/2018 | Nakatsuru et al. |

FOREIGN PATENT DOCUMENTS

| | | |
|---|---|---|
| EP | 2 993 191 A1 | 3/2016 |
| EP | 2 998 325 A1 | 3/2016 |
| JP | H03-227301 A | 10/1991 |
| JP | 2003-290290 A | 10/2003 |
| JP | 2007-154350 A | 6/2007 |
| JP | 2014-098172 A | 5/2014 |
| WO | WO 2016/006132 A1 | 1/2016 |
| WO | WO 2016-111223 A1 | 7/2016 |

OTHER PUBLICATIONS

International Search Report, in International Application No. PCT/JP2018/007959, dated Jun. 5, 2018 (in 2 pages).
English Translation of the Written Opinion of the International Searching Authority in International Application No. PCT/JP2018/007959, dated Jun. 5, 2018.
Supplementary European Search Report, European Patent Application No. 18 76 1143.9 dated Nov. 9, 2020.

*Primary Examiner* — Edward M Johnson
(74) *Attorney, Agent, or Firm* — Knobbe, Martens, Olson & Bear, LLP

(57) ABSTRACT

A water-absorbent resin that exhibits a high liquid-retention capacity under a load and a small amount of re-wet, even when it is used in an absorbent material having a low proportion of hydrophilic fibers. The water-absorbent resin includes a polymer of a water-soluble ethylenically unsaturated monomer, wherein when a cross-sectional image of the water-absorbent resin is observed using X-ray computed tomography, the water-absorbent resin has cavity area percentage in the cross-sectional image of 10% or less.

5 Claims, 1 Drawing Sheet

WATER-ABSORBENT RESIN AND ABSORBENT ARTICLE

TECHNICAL FIELD

The present invention relates to a water-absorbent resin and an absorbent article; more particularly, the present invention relates to a water-absorbent resin that constitutes an absorbent material suitably used for hygienic materials such as disposable diapers, sanitary napkins, and incontinence pads, and to an absorbent article comprising the water-absorbent resin.

BACKGROUND ART

In recent years, water-absorbent resins have been widely used in the field of hygienic materials such as disposable diapers, sanitary napkins, and incontinence pads.

As such water-absorbent resins, cross-linked products of partially neutralized acrylic acid polymers have been proposed as preferable water-absorbent resins, because they have many advantages, for example, as follows: they have good water-absorption capacity, and acrylic acid used as a raw material is readily industrially available, and thus, they can be produced at low cost with uniform quality; additionally, they are resistant to decomposition or degradation (see, for example, Patent Literature 1).

An absorbent article such as a disposable diaper, a sanitary napkin, or an incontinence pad is composed of an absorbent material that absorbs and retains a body liquid such as urine or menses excreted from the body, the absorbent material being positioned mainly in a central portion, a liquid-permeable front sheet (top sheet) positioned on the side of the absorbent article that is brought into contact with the body, and a liquid-impermeable rear sheet (back sheet) positioned opposite to the side that is brought into contact with the body. The absorbent material is composed of hydrophilic fibers such as pulp and a water-absorbent resin.

Conventionally, there has been an increasing demand for thinner and lighter absorbent articles from the viewpoint of design, convenience in carrying, and efficiency in distribution. Furthermore, in recent years, from the viewpoint of environmental conservation, there has been a growing need for a so-called eco-friendly intention to effectively utilize resources, and minimize the use of natural materials that require a long time to grow, such as trees. Examples of common methods for reducing the thickness of such an absorbent article include a method in which the amount of a water-absorbent resin is increased while reducing the amount of hydrophilic fibers, such as crushed pulp from wood, that serve to fix the water-absorbent resin in the absorbent material. Moreover, extensive research has been conducted on absorbent laminates, water-absorbent sheets, and the like that are substantially free of hydrophilic fibers within the absorbent layer.

CITATION LIST

Patent Literature

Patent Literature 1: JP H3-227301 A

SUMMARY OF INVENTION

Technical Problem

An absorbent material having a reduced proportion of hydrophilic fibers and an increased proportion of a water-absorbent resin is preferable for achieving a smaller thickness, from the viewpoint of reducing the bulky hydrophilic fibers, and retaining a liquid. However, in situations where a water-absorbent sheet including the water-absorbent resin is subjected to a load due to a deformation, a pressure, or the like, such as in a situation where an infant wearing a thinned absorbent article is sitting, the absorbent article may not sufficiently prevent re-wet (liquid re-wet) of the liquid to be absorbed. Furthermore, the absorbent article may not tolerate a plurality of discharges of urine, possibly causing discomfort to the wearer.

It is a main object of the present invention to provide a water-absorbent resin that exhibits a high liquid-retention capacity under a load and a small amount of re-wet even when it is used in an absorbent material having a low proportion of hydrophilic fibers.

Solution to Problem

The inventors of the present invention conducted a diligent study to solve the aforementioned problem. As a result, they found that a water-absorbent resin comprising a polymer of a water-soluble ethylenically unsaturated monomer, wherein when a cross-sectional image of the water-absorbent resin is observed using X-ray computed tomography, the water-absorbent resin has a ratio of the area of cavity portions (cavity area ratio) in the cross-sectional image of 10% or less, as calculated according to Equation (I) shown below, exhibits a high liquid-retention capacity under a load and a small amount of re-wet even when it is used in an absorbent material having a low proportion of hydrophilic fibers.

$$\text{Cavity area ratio}[\%] = \{\text{total cross-sectional area of cavity portions}(B) \text{ in the water-absorbent resin} / (\text{total cross-sectional area of resin portions}(A) \text{ in the water-absorbent resin} + \text{total cross-sectional area of cavity portions}(B) \text{ in the water-absorbent resin})\} \times 100 \quad (I).$$

The present invention has been accomplished as a result of further study based on these findings.

In summary, the present invention provides aspects of the invention comprising the following features:

Item 1. A water-absorbent resin comprising a polymer of a water-soluble ethylenically unsaturated monomer, wherein when a cross-sectional image of the water-absorbent resin is observed using X-ray computed tomography, the water-absorbent resin has a ratio of the area of cavity portions (cavity area ratio) in the cross-sectional image of 10% or less, as calculated according to Equation (I):

$$\text{cavity area ratio}[\%] = \{\text{total cross-sectional area of cavity portions}(B) \text{ in the water-absorbent resin} / (\text{total cross-sectional area of resin portions}(A) \text{ in the water-absorbent resin} + \text{total cross-sectional area of cavity portions}(B) \text{ in the water-absorbent resin})\} \times 100 \quad (1).$$

Item 2. The water-absorbent resin according to item 1, wherein the water-absorbent resin has a physiological saline-retention ratio under a load of 73% or more.

Item 3. The water-absorbent resin according to item 1 or 2, wherein the water-absorbent resin has a substantially spherical shape or a shape in which particles having a substantially spherical shape are aggregated.

Item 4. The water-absorbent resin according to any one of items 1 to 3, which is used in an absorbent material designed to have a proportion of hydrophilic fibers of 50% by mass or less in the absorbent material.

Advantageous Effects of Invention

In accordance with the present invention, there is provided a water-absorbent resin that exhibits a high liquid-retention capacity under a load and a small amount of re-wet even when it is used in an absorbent material having a low proportion of hydrophilic fibers. Furthermore, in accordance with the present invention, there is provided an absorbent article comprising the water-absorbent resin.

DESCRIPTION OF EMBODIMENTS

1. Water-Absorbent Resin

A water-absorbent resin according to the present invention comprises a polymer of a water-soluble ethylenically unsaturated monomer, wherein when a cross-sectional image of the water-absorbent resin is observed using X-ray computed tomography, the water-absorbent resin has a ratio of the area of cavity portions (cavity area ratio) in the cross-sectional image of 10% or less, as calculated according to Equation (I):

cavity area ratio[%]={total cross-sectional area of cavity portions(B)in the water-absorbent resin/(total cross-sectional area of resin portions(A)in the water-absorbent resin+total cross-sectional area of cavity portions(B)in the water-absorbent resin)}×100     (I).

The water-absorbent resin of the present invention comprising these features is characterized by exhibiting a high liquid-retention capacity under a load and a small amount of re-wet even when it is used in an absorbent material having a low proportion of hydrophilic fibers (including an absorbent material not containing hydrophilic fibers). The water-absorbent resin of the present invention will be hereinafter described in detail.

Figure 2:
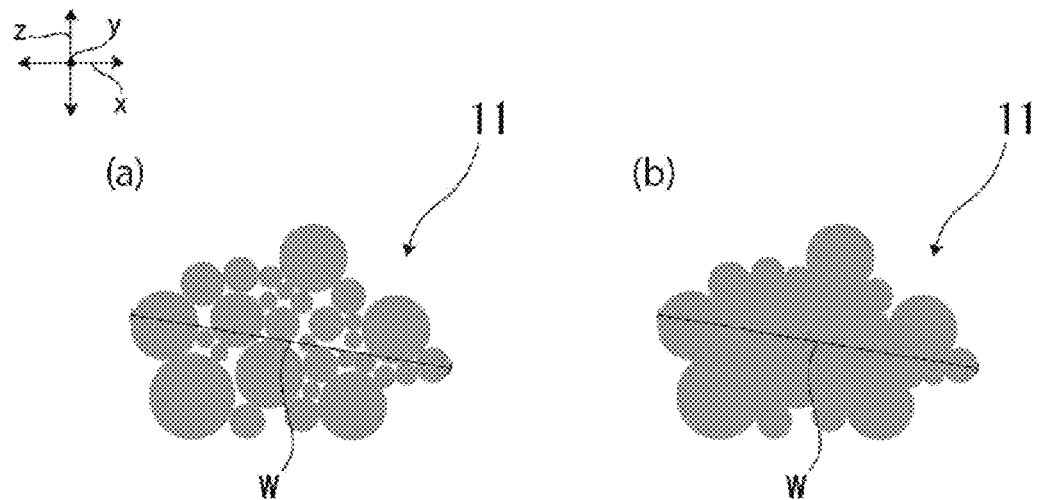
FIG. 2(a) is a schematic diagram of a cross-sectional image of a water-absorbent resin taken using X-ray computed tomography.
FIG. 2(b) is a schematic diagram prepared by filling the cavity portions shown in the schematic diagram of FIG. 2(a).

As used herein, the phrase "total cross-sectional area of resin portions in the water-absorbent resin" refers to the total cross-sectional area of portions where the water-absorbent resin is present (filled portions) in the cross-sectional image of the water-absorbent resin, as shown in the schematic diagram of FIG. 2(a), for example. The phrase "total cross-sectional area of cavity portions in the water-absorbent resin" refers to the total area of cavity portions in the water-absorbent resin (blank portions in the water-absorbent resin) in the cross-sectional image of the water-absorbent resin, as shown in the schematic diagram of FIG. 2(a), for example.

Examples of shapes of the water-absorbent resin of the present invention include a substantially spherical shape, a shape in which particles having a substantially spherical shape are aggregated, a crushed indefinite shape, a shape in which particles having a crushed indefinite shape are aggregated, and a flat shape. Through the use of reversed phase suspension polymerization or spray droplet polymerization, a water-absorbent resin having a substantially spherical particle shape, such as a spherical or elliptical shape, or a shape in which particles having a substantially spherical shape are aggregated, can be produced. Through the use of aqueous solution polymerization, a water-absorbent resin having a crushed indefinite shape or a shape in which particles having a crushed indefinite shape are aggregated can be produced. From the viewpoint of controlling the cavity area ratio, preferred as the shape of the water-absorbent resin is a substantially spherical shape or a shape in which particles having a substantially spherical shape are aggregated.

When a cross-sectional image of the water-absorbent resin is observed using X-ray computed tomography, the water-absorbent resin has a ratio of the area of cavity portions (cavity area ratio) in the cross-sectional image of 10% or less, as calculated according to Equation (1) above. The cavity area ratio is, for example, preferably 0.5 to 8%, and more preferably 1 to 6%, from the viewpoint of achieving a water-absorbent resin that exhibits a higher liquid-retention capacity under a load and a smaller amount of re-wet even when it is used in an absorbent material having a low proportion of hydrophilic fibers.

It is believed that in the water-absorbent resin of the present invention, because the cavity area ratio is adjusted to 10% or less, the amount of the liquid retained in cavity portions (gap portions) of the water-absorbent resin is small, such that the liquid is favorably absorbed by the water-absorbent resin, and as a result, the water-absorbent resin of the present invention exhibits a high liquid-retention capacity under a load, and effectively reduces the amount of re-wet from the cavity portions. As described above, from the viewpoint of reducing the thickness of an absorbent article including a water-absorbent resin, it may be possible to use an absorbent material having a reduced proportion of hydrophilic fibers and an increased proportion of a water-absorbent resin. However, in the case where such a thinned absorbent article is used as, for example, a water-absorbent sheet, if the absorbent material is subjected to a load due to a deformation, a pressure, or the like, the water-absorbent sheet cannot sufficiently prevent re-wet (liquid re-wet) of the liquid (liquid to be absorbed). In contrast, because the water-absorbent resin of the present invention exhibits a high liquid-retention capacity under a load, and effectively reduces the amount of re-wet, it can be suitably used in an absorbent article including an absorbent material having a low proportion of hydrophilic fibers and a high proportion of the water-absorbent resin.

In the present invention, the cavity area ratio is measured as follows, using X-ray computed tomography.

<Measurement of Cavity Area Ratio Using X-Ray Computed Tomography>

Particles of the water-absorbent resin are classified in advance with JIS standard sieves. Four particles are randomly selected from particles of the water-absorbent resin on a sieve with a mesh size of 180 μm that pass through a sieve with a mesh size of 600 μm, and these particles are used as resin samples. The resin samples are placed on a sample stage of an X-ray computed tomography apparatus, and cross-sectional image data are acquired using X-ray computed tomography. Next, for each of the resin samples, shapes at given angles or given horizontal and vertical cross sections are observed using image analysis software.

Figure 1:
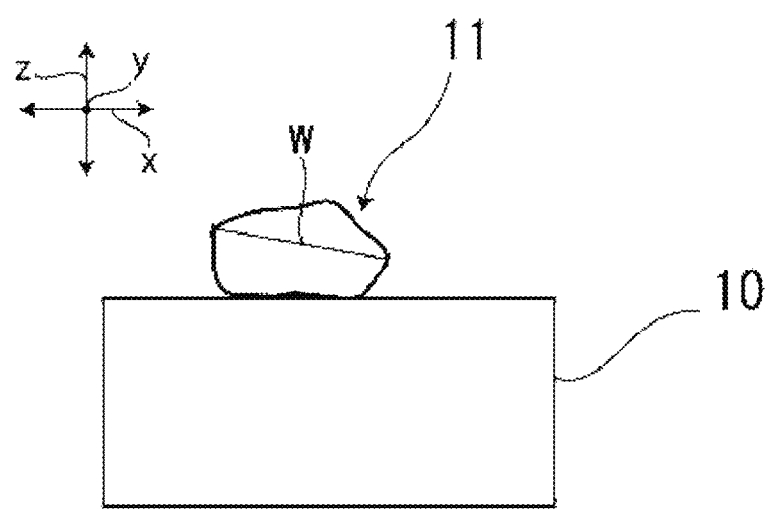
FIG. 1 is a schematic diagram for use in illustrating a method for measuring the cavity area ratio of a water-absorbent resin using X-ray computed tomography.

Here, from given cross sections in horizontal directions (x- and y-directions) and a vertical direction (z-direction) with respect to the mounting surface of the sample stage, a horizontal or vertical cross-sectional image having a maximum distance between given two points on the contour of each of the resin samples is selected. Specifically, as shown in the schematic diagram of FIG. 1, for each of the three directions, x-, y-, and z-directions, that are perpendicular to one another, cross-sectional images of a resin sample 11 on a sample stage 10 are acquired first. Subsequently, for each of these directions, one cross-sectional image having the longest particle length w (see FIGS. 1 and 2) of the resin sample (i.e., a cross-sectional image taken in a position where the particle length of the resin sample is the longest) is selected. Then, a cross-sectional image having the longest particle length w of the resin sample of these three cross-sectional images is selected.

Next, the cavity area ratio is calculated using this cross-sectional image. By means of general-purpose image processing software, the cross-sectional area of the resin sample (total cross-sectional area of resin portions (A) in the water-absorbent resin) (the area of the filled portions in the schematic diagram of FIG. 2(a)) and the cross-sectional area of the cross section of the resin sample in which cavities are filled (the area of the filled portion in the schematic diagram of FIG. 2(b)) are measured. The cross-sectional area of cavity portions in the resin sample (total cross-sectional area of cavity portions (B) in the water-absorbent resin) is calculated by subtracting the cross-sectional area of the resin sample from the cross-sectional area of the resin sample in which cavities are filled. Then, the cavity area ratio of the resin sample is calculated according to Equation (I) shown below. Using this method, the cavity area ratio of the resin sample is measured for each of the four resin samples, and the average value thereof is determined as the cavity area ratio of the water-absorbent resin.

Cavity area ratio[%]={total cross-sectional area of cavity portions(B)in the water-absorbent resin/(total cross-sectional area of resin portions(A)in the water-absorbent resin+total cross-sectional area of cavity portions(B)in the water-absorbent resin)}×100  (1).

The method for measuring the cavity area ratio using X-ray computed tomography is more specifically described in the Examples.

The water-absorbent resin of the present invention preferably has a median particle diameter of 200 to 600 μm, more preferably 250 to 500 μm, still more preferably 300 to 450 μm, and even more preferably 350 to 450 μm.

The median particle diameter of the water-absorbent resin can be measured using JIS standard sieves. More specifically, the median particle diameter represents a value as measured using the method described in the Examples.

From the viewpoint of achieving a water-absorbent resin that exhibits a higher liquid-retention capacity under a load and a smaller amount of re-wet even when it is used in an absorbent material having a low proportion of hydrophilic fibers, the water-absorbent resin of the present invention preferably has a physiological saline-retention ratio under a load of 73% or more, more preferably 74 to 90%, and still more preferably 75 to 85%.

The physiological saline-retention ratio under a load of the water-absorbent resin is measured by subjecting the water-absorbent resin that has absorbed physiological saline to a load of 21 g/cm$^2$. More specifically, the physiological saline-retention ratio under a load represents a value as measured using the method described in the Examples.

The water-absorbent resin of the present invention may contain additives suitable for its purpose. Examples of such additives include inorganic powders, surfactants, oxidizing agents, reducing agents, metal chelating agents, radical chain inhibitors, antioxidants, anti-bacterial agents, and deodorizers. For example, when 0.05 to 5 parts by mass of amorphous silica as an inorganic powder is added to 100 parts by mass of the water-absorbent resin, the flowability of the water-absorbent resin can be improved.

The water-absorbent resin of the present invention is characterized by exhibiting a high liquid-retention capacity under a load and a small amount of re-wet even when it is used in an absorbent material having a low proportion of hydrophilic fibers; therefore, as described above, the water-absorbent resin of the present invention constitutes an absorbent material together with hydrophilic fibers, and can be suitably used in an absorbent material designed to have a proportion of the hydrophilic fibers that is preferably 50% by mass or less, and more preferably 0 to 30% by mass or less, in the absorbent material.

Furthermore, because the water-absorbent resin of the present invention has the above-described characteristics, it can be suitably used in thin absorbent articles (for example, those in which the absorbent material has a thickness that is preferably 5 mm or less, and more preferably 3 mm or less).

2. Method for Producing Water-Absorbent Resin

The water-absorbent resin of the present invention can be produced by polymerizing a water-soluble ethylenically unsaturated monomer.

To polymerize the water-soluble ethylenically unsaturated monomer, a representative polymerization method such as aqueous solution polymerization, spray droplet polymerization, emulsion polymerization, or reversed phase suspension polymerization is used. In aqueous solution polymerization, polymerization is performed by heating, optionally with stirring, an aqueous solution of the water-soluble ethylenically unsaturated monomer. Examples of methods for controlling the cavity area ratio in aqueous solution polymerization include a method in which a foaming agent, for example, is added to the water-soluble ethylenically unsaturated monomer; and a method in which particles of a water-absorbent resin obtained by aqueous solution polymerization are aggregated. In reversed phase suspension polymerization, polymerization is performed by heating the water-soluble ethylenically unsaturated monomer with stirring in a hydrocarbon dispersion medium. Examples of methods for controlling the cavity area ratio in reversed phase suspension polymerization include a method in which a foaming agent, for example, is added to the first-stage water-soluble ethylenically unsaturated monomer; a method in which the median particle diameter of primary particles obtained in the first-stage reversed phase suspension polymerization is controlled; and a method in which a hydrous gel obtained after the first-stage polymerization is further heated. In the present invention, reversed phase suspension polymerization is preferred from the viewpoint of allowing the polymerization reaction to be precisely controlled, and a wide range of particle diameters to be controlled.

One exemplary method for producing the water-absorbent resin of the present invention will be hereinafter described.

Examples of methods for producing the water-absorbent resin include a method for producing the water-absorbent resin by performing reversed phase suspension polymerization of the water-soluble ethylenically unsaturated monomer in a hydrocarbon dispersion medium, the method including the steps of:

performing the polymerization in the presence of a radical polymerization initiator; and post-crosslinking the hydrous gel obtained by the polymerization in the presence of a post-crosslinking agent.

In the method for producing the water-absorbent resin of the present invention, an internal-crosslinking agent may be added, as required, to the water-soluble ethylenically unsaturated monomer to obtain a hydrous gel having an internally crosslinked structure.

<Polymerization Step>

[Water-Soluble Ethylenically Unsaturated Monomer]

Examples of the water-soluble ethylenically unsaturated monomer include (meth)acrylic acid ("acryl" and "methacryl" are herein collectively referred to as "(meth)acryl"; the same applies below) and salts thereof; 2-(meth)acrylamido-2-methylpropanesulfonic acid and salts thereof; nonionic monomers such as (meth)acrylamide, N,N-dimethyl (meth)acrylamide, 2-hydroxyethyl(meth)acrylate, N-methylol(meth)acrylamide, and polyethylene glycol mono(meth)acrylate; and amino group-containing unsaturated monomers such as N,N-diethyl aminoethyl(meth)acrylate, N,N-diethylaminopropyl(meth)acrylate, and diethylaminopropyl(meth)acrylamide, as well as quaternary compounds thereof. Preferred among these water-soluble ethylenically unsaturated monomers are (meth)acrylic acid and salts thereof, (meth)acrylamide, and N,N-dimethyl (meth)acrylamide, and more preferred are (meth)acrylic acid and salts thereof, from the viewpoint of being readily industrially available. These water-soluble ethylenically unsaturated monomers may be used alone or in combination of two or more.

Among these water-soluble ethylenically unsaturated monomers, acrylic acid and salts thereof are widely used as raw materials of water-absorbent resins. Copolymers of acrylic acid and/or salts thereof with other water-soluble ethylenically unsaturated monomers as mentioned above may also be used. In this case, an acrylic acid and/or a salt thereof as a main water-soluble ethylenically unsaturated monomer is preferably used in an amount of 70 to 100 mol % based on the total amount of water-soluble ethylenically unsaturated monomers.

The water-soluble ethylenically unsaturated monomer is preferably dispersed as an aqueous solution in a hydrocarbon dispersion medium, and then subjected to reversed phase suspension polymerization. When the water-soluble ethylenically unsaturated monomer is in the form of an aqueous solution, the dispersion efficiency in the hydrocarbon dispersion medium can be increased. The concentration of the water-soluble ethylenically unsaturated monomer in the aqueous solution is preferably in the range of 20% by mass to not more than the saturation concentration. The concentration of the water-soluble ethylenically unsaturated monomer is more preferably 55% by mass or less, still more preferably 50% by mass or less, and even more preferably 45% by mass or less. On the other hand, the concentration of the water-soluble ethylenically unsaturated monomer is more preferably 25% by mass or more, still more preferably 28% by mass or more, and even more preferably 30% by mass or more.

When the water-soluble ethylenically unsaturated monomer has an acid group such as (meth)acrylic acid or 2-(meth)acrylamido-2-methylpropanesulfonic acid, the acid group may be neutralized with an alkaline neutralizing agent, as required, before use. Examples of such alkaline neutralizing agents include alkali metal salts such as sodium hydroxide, sodium carbonate, sodium hydrogen carbonate, potassium hydroxide, and potassium carbonate; and ammonia. These alkaline neutralizing agents may be used in the form of aqueous solutions to facilitate the neutralization operation. The above-mentioned alkaline neutralizing agents may be used alone or in combination of two or more.

The degree of neutralization of the water-soluble ethylenically unsaturated monomer with an alkaline neutralizing agent, calculated as the degree of neutralization of all acid groups in the water-soluble ethylenically unsaturated monomer, is preferably 10 to 100 mol %, more preferably 30 to 90 mol %, still more preferably 40 to 85 mol %, and even more preferably 50 to 80 mol %.

[Radical Polymerization Initiator]

Examples of the radical polymerization initiator to be added in the polymerization step include persulfates such as potassium persulfate, ammonium persulfate, and sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxyisobutyrate, t-butyl peroxypivalate, and hydrogen peroxide; and azo compounds such as 2,2'-azobis(2-amidinopropane) dihydrochloride, 2,2'-azobis[2-(N-phenylamidino)propane] dihydrochloride, 2,2'-azobis[2-(N-allylamidino)propane] dihydrochloride, 2,2'-azobis {(2-[1-(2-hydroxyethyl)-2-imidazolin-2-yl]propane} dihydrochloride, 2,2'-azobis(2-methyl-N-[1,1-bis(hydroxymethyl)-2-hydroxyethyl]propionamide), 2,2'-azobis[2-methyl-N-(2-hydroxyethyl)-propionamide], and 4,4'-azobis(4-cyanovaleric acid). Preferred among these radical polymerization initiators are potassium persulfate, ammonium persulfate, sodium persulfate, and 2,2'-azobis(2-amidinopropane) dihydrochloride, from the viewpoint of being readily available and easy to handle. These radical polymerization initiators may be used alone or in combination of two or more.

The above-mentioned radical polymerization initiators may also be used in combination with reducing agents such as sodium sulfite, sodium hydrogensulfite, ferrous sulfate, and L-ascorbic acid to be used as redox polymerization initiators.

The amount of the radical polymerization initiator to be used may be, for example, 0.00005 to 0.01 mol per mole of the water-soluble ethylenically unsaturated monomer, although not limited thereto. The use of the radical polymerization initiator in the above-defined range of amounts can avoid the occurrence of an abrupt polymerization reaction, and can complete the polymerization reaction in an appropriate time.

[Internal-Crosslinking Agent]

Examples of the internal-crosslinking agent include those that can crosslink the polymer of the water-soluble ethylenically unsaturated monomer to be used, for example: unsaturated polyesters obtained by reacting polyols such as diols and triols, e.g., (poly)ethylene glycol["(poly)" means both cases with and without the prefix "poly"; the same applies below], (poly)propylene glycol, 1,4-butanediol, trimethylolpropane, and (poly)glycerin, with unsaturated acids such as (meth)acrylic acid, maleic acid, and fumaric acid; bisacrylamides such as N,N-methylenebisacrylamide; di or tri(meth)acrylic acid esters obtained by reacting polyepoxides with (meth)acrylic acid; carbamyl di(meth)acrylates obtained by reacting polyisocyanates such as tolylene diisocyanate and hexamethylene diisocyanate with hydroxyethyl (meth)acrylate; compounds having two or more polymerizable unsaturated groups such as allylated starch, allylated cellulose, diallyl phthalate, N,N',N"-triallylisocyanate, and divinylbenzene; polyglycidyl compounds such as diglycidyl compounds and triglycidyl compounds, e.g., (poly)ethylene glycol diglycidyl ether, (poly)propylene glycol diglycidyl ether, and (poly)glycerin diglycidyl ether; epihalohydrin compounds such as epichlorohydrin, epibromohydrin, and α-methylepichlorohydrin; compounds having two or more reactive functional groups such as isocyanate compounds, e.g., 2,4-tolylene diisocyanate and hexamethylene diisocyanate; and oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, and 3-butyl-3-oxetaneethanol. Among these internal-crosslinking agents, polyglycidyl compounds are preferably used, diglycidyl ether compounds are more preferably used, and (poly)ethylene glycol diglycidyl ether, (poly)propylene glycol diglycidyl ether, and (poly)glycerin diglycidyl ether are still more preferably used. These internal-crosslinking agents may be used alone or in combination of two or more.

The amount of the internal-crosslinking agent to be used is preferably 0.000001 to 0.02 mol, more preferably 0.00001 to 0.01 mol, still more preferably 0.00001 to 0.005 mol, and even more preferably 0.00001 to 0.002 mol, per mole of the water-soluble ethylenically unsaturated monomer.

[Hydrocarbon Dispersion Medium]

Examples of the hydrocarbon dispersion medium include $C_{6-8}$ aliphatic hydrocarbons such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, and xylene. Among these hydrocarbon dispersion media, n-hexane, n-heptane, and cyclohexane, which are readily industrially available, stable in quality, and inexpensive, are particularly suitably used. These hydrocarbon dispersion media may be used alone or in combination of two or more. Examples of mixtures of hydrocarbon dispersion media include commercially available products such as Exxsol Heptane (Exxon Mobil Corporation; containing 75 to 85% by mass of heptane and its isomeric hydrocarbons). The use of such a mixture also leads to favorable results.

The amount of the hydrocarbon dispersion medium to be used is preferably 100 to 1500 parts by mass, and more preferably 200 to 1400 parts by mass, per 100 parts by mass of the first-stage water-soluble ethylenically unsaturated monomer, from the viewpoint of homogeneously dispersing the water-soluble ethylenically unsaturated monomer, and facilitating control of the polymerization temperature. As described below, reversed phase suspension polymerization is performed in a single stage or two or more multiple stages. The first-stage polymerization as mentioned above refers to the first-stage polymerization reaction in single-stage polymerization or multi-stage polymerization (the same applies below).

[Dispersion Stabilizer]

(Surfactant)

In reversed phase suspension polymerization, a dispersion stabilizer may be used to improve the dispersion stability of the water-soluble ethylenically unsaturated monomer in the hydrocarbon dispersion medium. A surfactant may be used as such a dispersion stabilizer.

Examples of the surfactant include sucrose fatty acid esters, polyglycerin fatty acid esters, sorbitan fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hydrogenated castor oil, alkyl allyl formaldehyde condensate polyoxyethylene ethers, polyoxyethylene-polyoxypropylene block copolymers, polyoxyethylene polyoxypropyl alkyl ethers, polyethylene glycol fatty acid esters, alkyl glucosides, N-alkyl glyconamides, polyoxyethylene fatty acid amides, polyoxyethylene alkylamines, polyoxyethylene alkyl ether phosphates, and polyoxyethylene alkyl allyl ether phosphates. Among these surfactants, sucrose fatty acid esters, polyglycerin fatty acid esters, and sorbitan fatty acid esters are particularly preferably used, from the viewpoint of dispersion stability of the monomer. These surfactants may be used alone or in combination of two or more.

The amount of the surfactant to be used is preferably 0.1 to 30 parts by mass, and more preferably 0.3 to 20 parts by mass, per 100 parts by mass of the first-stage water-soluble ethylenically unsaturated monomer.

(Polymeric Dispersion Agent)

A polymeric dispersion agent may be used in combination with the above-described surfactant, as a dispersion stabilizer to be used in reversed phase suspension polymerization.

Examples of the polymeric dispersion agent include maleic anhydride modified polyethylene, maleic anhydride modified polypropylene, maleic anhydride modified ethylene-propylene copolymers, maleic anhydride modified EPDM (ethylene-propylene-diene terpolymers), maleic anhydride modified polybutadiene, maleic anhydride-ethylene copolymers, maleic anhydride-propylene copolymers, maleic anhydride-ethylene-propylene copolymers, maleic anhydride-butadiene copolymers, polyethylene, polypropylene, ethylene-propylene copolymers, oxidized polyethylene, oxidized polypropylene, oxidized ethylene-propylene copolymers, ethylene-acrylic acid copolymers, ethyl cellulose, and ethyl hydroxyethyl cellulose. Among these polymeric dispersion agents, maleic anhydride modified polyethylene, maleic anhydride modified polypropylene, maleic anhydride modified ethylene-propylene copolymers, maleic anhydride-ethylene copolymers, maleic anhydride-propylene copolymers, maleic anhydride-ethylene-propylene copolymers, polyethylene, polypropylene, ethylene-propylene copolymers, oxidized polyethylene, oxidized polypropylene, and oxidized ethylene-propylene copolymers are particularly preferably used, from the viewpoint of dispersion stability of the monomer. These polymeric dispersion agents may be used alone or in combination of two or more.

The amount of the polymeric dispersion agent to be used is preferably 0.1 to 30 parts by mass, and more preferably 0.3 to 20 parts by mass, per 100 parts by mass of the first-stage water-soluble ethylenically unsaturated monomer.

[Other Components]

In the method for producing the water-absorbent resin, other components may be added, as desired, to the aqueous solution containing the water-soluble ethylenically unsaturated monomer to be subjected to reversed phase suspension polymerization. Various additives such as thickeners, foaming agents, and chain transfer agents may be added as other components.

(Thickener)

By way of example, a thickener may be added to the aqueous solution containing the water-soluble ethylenically unsaturated monomer to be subjected to reversed phase suspension polymerization. When a thickener is thus added to adjust the viscosity of the aqueous solution, the median particle diameter of the particles obtained by reversed phase suspension polymerization can be controlled.

Examples of usable thickeners include hydroxyethylcellulose, hydroxypropylcellulose, methylcellulose, carboxymethylcellulose, polyacrylic acid, (partially) neutralized polyacrylic acid, polyethylene glycol, polyacrylamide, polyethyleneimine, dextrin, sodium alginate, polyvinyl alcohol, polyvinylpyrrolidone, and polyethylene oxide. For a fixed stirring rate during the polymerization, the higher the viscosity of the aqueous solution containing the water-soluble ethylenically unsaturated monomer, the larger the median particle diameter of the primary particles and/or secondary particles of the resulting particles tends to be.

(Foaming Agent)

By way of example, a foaming agent may be added to the aqueous solution containing the water-soluble ethylenically unsaturated monomer to be subjected to reversed phase suspension polymerization. When a foaming agent is thus added to introduce foam into the aqueous solution, the cavity area ratio of the particles obtained by reversed phase suspension polymerization can be controlled. Various foaming agents such as carbonates and hydrogencarbonates may be used as the foaming agent.

[Reversed Phase Suspension Polymerization]

To perform reversed phase suspension polymerization, for example, the aqueous solution containing the water-soluble ethylenically unsaturated monomer is dispersed in a hydrocarbon dispersion medium, in the presence of a dispersion stabilizer. Here, so long as the dispersion stabilizer (a surfactant or a polymeric dispersion agent) is added before the beginning of the polymerization reaction, it may be added either before or after the aqueous monomer solution is dispersed in the hydrocarbon dispersion medium.

In particular, from the viewpoint of readily reducing the amount of remaining hydrocarbon dispersion medium in the resulting water-absorbent resin, it is preferred to disperse the aqueous monomer solution in the hydrocarbon dispersion medium in which a polymeric dispersion agent is dispersed, followed by dispersing a surfactant therein, and then perform polymerization.

Such reversed phase suspension polymerization can be performed in a single stage or two or more multiple stages. From the viewpoint of enhancing productivity, reversed phase suspension polymerization is preferably performed in two or three stages.

Reversed phase suspension polymerization with two or more multiple stages may be performed as follows: the first-stage reversed phase suspension polymerization is performed; subsequently, a water-soluble ethylenically unsaturated monomer is added to the reaction mixture obtained by the first-stage polymerization reaction and mixed, and reversed phase suspension polymerization in the second and subsequent stages is performed in the same manner as in the first stage. In reversed phase suspension polymerization in each of the second and subsequent stages, in addition to the water-soluble ethylenically unsaturated monomer, a radical polymerization initiator is preferably added within the above-described range of molar ratios of each of the components relative to the water-soluble ethylenically unsaturated monomer, based on the amount of the water-soluble ethylenically unsaturated monomer added during reversed phase suspension polymerization in each of the second and subsequent stages. In the second and subsequent stages of polymerization, an internal-crosslinking agent may also be added, as required, to the water-soluble ethylenically unsaturated monomer.

The reaction temperature during the polymerization reaction is preferably 20 to 110° C., and more preferably 40 to 90° C., from the viewpoint of allowing the polymerization to proceed quickly to reduce the polymerization time for improved economical efficiency, and readily removing the heat of polymerization to perform a smooth reaction.

In the method for producing the water-absorbent resin of the present invention, the system in which the hydrous gel is dispersed in the hydrocarbon dispersion medium after the first-stage reversed phase suspension polymerization may be heated, as required, by applying external energy such as heat. The heating temperature is preferably 50 to 100° C., and more preferably 60 to 90° C. The heating time is preferably 0.1 to 3 hours.

The aqueous monomer solution may be stirred with any of various well-known stirring blades. Specific examples of usable stirring blades include propeller blades, paddle blades, anchor blades, turbin blades, Pfaudler blades, ribbon blades, FULLZONE blades (Shinko Pantec Co., Ltd.), MAXBLEND blades (Sumitomo Heavy Industries, Ltd.), and SUPERMIX blades (Satake Chemical Equipment Mfg., Ltd.). The median particle diameter of the primary particles obtained in the first-stage polymerization can be controlled by adjusting the stirring rate in the first-stage reversed phase suspension polymerization. The stirring rate can be adjusted by adjusting the rotation speed of a stirrer, for example.

In the method for producing the water-absorbent resin of the present invention, the above-described cavity area ratio can be controlled to 10% or less, by, for example, adjusting the amount of the radical polymerization initiator and the amount of the internal-crosslinking agent to be added to the water-soluble ethylenically unsaturated monomer during reversed phase suspension polymerization, by controlling the median particle diameter of the primary particles in the first-stage polymerization, and by heating the hydrous gel after the first-stage polymerization. These procedures may be performed alone or in combination.

<Post-Crosslinking Step>

The water-absorbent resin of the present invention may be obtained by post-crosslinking the hydrous gel having an internally crosslinked structure obtained by polymerizing the water-soluble ethylenically unsaturated monomer, using a post-crosslinking agent (post-crosslinking reaction). The post-crosslinking reaction is preferably preformed in the presence of a post-crosslinking agent, after the polymerization of the water-soluble ethylenically unsaturated monomer. When the hydrous gel having an internally crosslinked structure is thus subjected to the post-crosslinking reaction after the polymerization, a water-absorbent resin can be achieved in which the crosslinking density in the vicinity of the surface has been increased to improve various kinds of performance such as the water-absorption capacity under a load.

Examples of the post-crosslinking agent include compounds having two or more reactive functional groups, for example: polyols such as ethylene glycol, propylene glycol, 1,4-butanediol, trimethylolpropane, glycerin, polyoxyethylene glycol, polyoxypropylene glycol, and polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether; haloepoxy compounds such as epichlorohydrin, epibromohydrin, and α-methylepichlorohydrin; isocyanate compounds such as 2,4-tolylene diisocyanate and hexamethylene diisocyanate; oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, and 3-butyl-3-oxetaneethanol; oxazoline compounds such as 1,2-ethylenebisoxazoline; carbonate compounds such as ethylene carbonate; and hydroxyalkylamide compounds such as bis[N,N-di(β-hydroxyethyl)]adipamide. Preferred among these post-crosslinking agents are polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether. These post-crosslinking agents may be used alone or in combination of two or more.

The amount of the post-crosslinking agent to be used is preferably 0.00001 to 0.01 mol, more preferably 0.00005 to 0.005 mol, and still more preferably 0.0001 to 0.002 mol, per mole of the water-soluble ethylenically unsaturated monomer subjected to polymerization. When reversed phase suspension polymerization is performed in two or more multiple stages, the amount of the water-soluble ethylenically unsaturated monomer that serves as a basis of the amount of the post-crosslinking agent to be used corresponds to the total amount of the water-soluble ethylenically unsaturated monomer used in each of the stages.

The post-crosslinking agent may be added as is or as an aqueous solution. As required, a solution of the post-crosslinking agent in a hydrophilic organic solvent may be added. Examples of such hydrophilic organic solvents include lower alcohols such as methyl alcohol, ethyl alcohol, n-propyl alcohol, and isopropyl alcohol; ketones such as acetone and methyl ethyl ketone; ethers such as diethyl ether, dioxane, and tetrahydrofuran; amides such as N,N-dimethylformamide; and sulfoxides such as dimethylsulfoxide. These hydrophilic organic solvents may be used alone, in combination of two or more, or as a mixture with water.

The post-crosslinking agent may be added after the polymerization reaction of the water-soluble ethylenically unsaturated monomer is substantially completed. The post-crosslinking agent is preferably added in the presence of 1 to 400 parts by mass of water, more preferably 5 to 200 parts by mass of water, still more preferably 10 to 100 parts by mass of water, and even more preferably 20 to 60 parts by mass of water, per 100 parts by mass of the water-soluble ethylenically unsaturated monomer. The amount of water herein refers to the total amount of the water contained in the reaction system and the water that is used, as required, during the addition of the post-crosslinking agent.

The reaction temperature during the post-crosslinking reaction is preferably 50 to 250° C., more preferably 60 to 180° C., still more preferably 60 to 140° C. and even more preferably 70 to 120° C. The reaction time of the post-crosslinking reaction is preferably 1 to 300 minutes, and more preferably 5 to 200 minutes.

<Drying Step>

The method for producing the water-absorbent resin of the present invention may include, after performing reversed phase suspension polymerization as described above, a drying step of adding external energy such as heat to the system to remove the water, hydrocarbon dispersion medium, and the like from the system by distillation. To remove the water in the hydrous gel after reversed phase suspension polymerization, the system in which the hydrous gel is dispersed in the hydrocarbon dispersion medium is heated to distill the water and the hydrocarbon dispersion medium out of the system by azeotropic distillation. Here, if the distilled hydrocarbon dispersion medium only is returned into the system, continuous azeotropic distillation can be performed. In this case, the temperature within the system during drying is maintained at a temperature not higher than the azeotropic temperature with the hydrocarbon dispersion medium, which is preferable from the viewpoint of inhibiting deterioration of the resin. Subsequently, the water and the hydrocarbon dispersion medium are distilled off to obtain particles of the water-absorbent resin. By controlling the treatment conditions for the drying step after the polymerization to adjust the amount of water to be removed, various kinds of performance of the resulting water-absorbent resin can be controlled.

In the drying step, the drying treatment by distillation may be performed under atmospheric pressure or reduced pressure. The drying treatment may also be performed in a stream of nitrogen or the like, from the viewpoint of enhancing the drying efficiency. When the drying treatment is performed under atmospheric pressure, the drying temperature is preferably 70 to 250° C., more preferably 80 to 180° C., still more preferably 80 to 140° C., and even more preferably 90 to 130° C. When the drying treatment is performed under reduced pressure, the drying temperature is preferably 40 to 160° C., and more preferably 50 to 110° C.

When the post-crosslinking step with a post-crosslinking agent is performed after the polymerization of the monomer by reversed phase suspension polymerization, the drying step by distillation is performed as described above, after the completion of the post-crosslinking step.

Furthermore, various additives such as chelating agents, reducing agents, oxidizing agents, anti-bacterial agents, and deodorizers may be added, as required, to the water-absorbent resin, after polymerization, during drying, or after drying.

3. Absorbent Material and Absorbent Article

The water-absorbent resin of the present invention constitutes an absorbent material to be used for hygienic materials such as sanitary items and disposable diapers, and is suitably used for an absorbent article including the absorbent material.

Here, the absorbent material including the water-absorbent resin is composed of, for example, the water-absorbent resin and hydrophilic fibers. Examples of structures of the absorbent material include a mixed dispersion obtained by mixing the water-absorbent resin and hydrophilic fibers to give a homogeneous composition; a sandwich structure in which the water-absorbent resin is sandwiched between layered hydrophilic fibers; and a structure in which the water-absorbent resin and hydrophilic fibers are wrapped in tissue paper. The absorbent material may also contain other components such as thermally fusible synthetic fibers for enhancing the shape retention properties of the absorbent material, a hot melt adhesive, and an adhesive binder such as an adhesive emulsion. The water-absorbent resin of the present invention can also be used in an absorbent material that is substantially free of hydrophilic fibers (i.e., the content of hydrophilic fibers in the absorbent material is 0% by mass). Examples of absorbent materials substantially free of hydrophilic fibers include water-absorbent sheets.

The content of the water-absorbent resin in the absorbent material is preferably 50% by mass or more, and more preferably 70 to 100% by mass.

Examples of hydrophilic fibers include cellulose fibers such as cotton-like pulp made from wood, mechanical pulp, chemical pulp, and semi-chemical pulp; artificial cellulose fibers such as rayon and acetate; and fibers made of synthetic resins such as hydrophilized polyamide, polyester, and polyolefin.

As described above, the water-absorbent resin of the present invention is characterized by exhibiting a high liquid-retention capacity under a load and a small amount of re-wet even when it is used in an absorbent material having a low proportion of hydrophilic fibers; therefore, the water-absorbent resin of the present invention can constitute, together with hydrophilic fibers, an absorbent material that exhibits a high liquid-retention capacity under a load and a small amount of re-wet even when the proportion of the hydrophilic fibers in the absorbent material is preferably 50% by mass or less, and more preferably 0 to 30% by mass.

The absorbent material including the water-absorbent resin can be held between a liquid-permeable sheet (top sheet) that allows a liquid to pass through and a liquid-impermeable sheet (back sheet) that does not allow a liquid to pass through, to obtain an absorbent article. The liquid-permeable sheet is positioned on the side of the absorbent article that is brought into contact with the body, and the liquid-impermeable sheet is positioned opposite to the side that is brought into contact with the body.

Examples of the liquid-permeable sheet include air-through, spunbond, chemical bond, or needle punch non-woven fabrics made of fibers of polyethylene, polypropylene, polyester, or the like, and porous synthetic resin sheets. Examples of the liquid-impermeable sheet include synthetic resin films made of resins such as polyethylene, polypropylene, and polyvinyl chloride.

As described above, the water-absorbent resin of the present invention is characterized by exhibiting a high liquid-retention capacity under a load and a small amount of re-wet even when it is used in an absorbent material having a low proportion of hydrophilic fibers; therefore, when the water-absorbent resin of the present invention is used in an absorbent material, a thin absorbent article having a thickness that is preferably 5 mm or less, more preferably 3 mm or less, for example, can be achieved.

EXAMPLES

The present invention will be hereinafter described in detail by way of examples and comparative examples, although the present invention is not limited thereto.

Water-absorbent resins obtained in the following examples and comparative examples were evaluated using the tests described below. Each of the testing methods for evaluation will be hereinafter described.

<Measurement of Cavity Area Ratio Using X-ray Computed Tomography>

Particles of the water-absorbent resin were classified in advance with JIS standard sieves. Four particles were randomly selected from particles of the water-absorbent resin on a sieve with a mesh size of 180 μm that passed through a sieve with a mesh size of 600 μm, and these particles were used as resin samples. The resin samples were placed on a sample stage of an X-ray computed tomography apparatus (MicroXCT-400 from Xradia Inc.), and cross-sectional image data were acquired using X-ray computed tomography. Next, for each of the resin samples, shapes at given angles or given horizontal and vertical cross sections were observed using image analysis software (myVGL from Volume Graphics GmbH).

Here, from given cross sections in horizontal directions (x- and y-directions) and a vertical direction (z-direction) with respect to the mounting surface of the sample stage, a horizontal or vertical cross-sectional image having a maximum distance between given two points on the contour of each of the resin samples was selected. Specifically, as shown in the schematic diagram of FIG. 1, for each of the three directions, x-, y-, and z-directions, that are perpendicular to one another, cross-sectional images of a resin sample 11 on the sample stage 10 were acquired first. Subsequently, for each of these directions, one cross-sectional image having the longest particle length w (see FIGS. 1 and 2) of the resin sample (i.e., a cross-sectional image taken in a position where the particle length of the resin sample was the longest) was selected. Then, a cross-sectional image having the longest particle length w of the resin sample of these three cross-sectional images was selected.

More specifically, initially, cross sections (z-x sections) of slices of the resin sample were observed in y-direction while shifting the position in y-direction with respect to the mounting surface of the sample stage, and a z-x cross section having the longest particle length w of the resin sample (see FIGS. 1 and 2) was acquired. Similarly, cross sections (a z-y cross section and an x-y cross section) having the longest particle length w of the resin sample as observed in x- and z-directions were acquired. Then, a cross section having the longest particle length w of the resin sample of these three cross sections was selected.

Next, the cavity area ratio was calculated using this cross-sectional image. By means of general-purpose image processing software (NanoHunter NS2K-Pro/Lt from Nanosystem Corporation), the cross-sectional area of the resin sample (total cross-sectional area of resin portions (A) in the water-absorbent resin) (the area of the filled portions in the schematic diagram of FIG. 2(a)) and the cross-sectional area of the cross section of the resin sample in which cavities are filled (the area of the filled portion in the schematic diagram of FIG. 2(b)) were measured. The cross-sectional area of cavity portions in the resin sample (total cross-sectional area of cavity portions (B) in the water-absorbent resin) was calculated by subtracting the cross-sectional area of the resin sample from the cross-sectional area of the resin sample in which cavities are filled. Then, the cavity area ratio of the resin sample was calculated according to Equation (I) shown below. Using this method, the cavity area ratio of the resin sample was measured for each of the four resin samples, and the average value thereof was determined as the cavity area ratio of the water-absorbent resin.

$$\text{Cavity area ratio[\%]} = \{\text{total cross-sectional area of cavity portions}(B) \text{ in the water-absorbent resin} / (\text{total cross-sectional area of resin portions}(A) \text{ in the water-absorbent resin} + \text{total cross-sectional area of cavity portions}(B) \text{ in the water-absorbent resin})\} \times 100 \qquad (I).$$

The conditions for X-ray computed tomography were as follows:
Apparatus: MicroXCT-400 (Xradia Inc.)
X-ray tube voltage: 80 kV
X-ray tube current: 122 μA
Optical lens: 10 times
Irradiation time: 0.8 sec
Pixel size: 2.149 μm
X-ray source-to-sample distance: 29.1533 mm
Detector-to-sample distance: 7.3723 mm
Imaging range: −90° to 90°
Image analyzer: myVGL 2.2 (Volume Graphics GmbH)

<Median Particle Diameter>

JIS standard sieves having mesh sizes of 850 μm, 600 μm, 500 μm, 425 μm, 300 μm, 250 μm, and 150 μm, and a receiving tray were combined in that order from the top.

50 g of the water-absorbent resin was placed on the top sieve of the combined sieves, and shaken for 20 minutes with a Ro-Tap shaker to conduct classification. After the classification, the particle size distribution was determined by calculating the mass of the water-absorbent resin remaining on each sieve as the mass percentage relative to the total mass. Based on this particle size distribution, the mass percentage of the water-absorbent resin remaining on each sieve was integrated in descending order of mesh size. Thereby, the relationship between the sieve mesh size and the integrated value of the mass percentage of the water-absorbent resin remaining on each sieve was plotted on logarithmic probability paper. The plots on the probability paper were connected with straight lines, and a particle diameter equivalent to 50% by mass of the integrated mass percentage was determined as the median particle diameter.

<Physiological Saline-Retention Capacity>

500 g of a 0.9% by mass aqueous solution of sodium chloride (physiological saline) was weighed out into a 500-ml beaker, and 2.0±0.001 g of the water-absorbent resin was dispersed therein with stirring using a magnetic stirrer bar (8 mm in diameter×30 mm, without a ring) at 600 rpm, so as not to form unswollen lumps. The dispersion was allowed to stand with stirring for 30 minutes, such that the water-absorbent resin was sufficiently swollen. The dispersion was subsequently poured into a cotton bag (Cottonbroad No. 60, 100 mm in width×200 mm in length), and the top of the cotton bag was closed with a rubber band. Then, the cotton bag was dehydrated for 1 minute using a dehydrator (product number: H-122 from Kokusan Co., Ltd.) set at a centrifugal force of 167 G, and the mass Wa (g) of the dehydrated cotton bag containing the swollen gel was measured. The same procedure was performed without adding the water-absorbent resin, and the mass Wb (g) of the empty cotton bag upon wetting was measured. The physiological saline-retention capacity of the water-absorbent resin was calculated according to the following equation:

Physiological saline-retention capacity$(g/g)$=[$Wa$−$Wb$]$(g)$/mass$(g)$ of the water-absorbent resin <Measurement of Physiological Saline-Retention Ratio Under a Load>

The physiological saline-retention ratio under a load was measured in a room adjusted to a temperature of 25° C.±1° C. 250 g of physiological saline adjusted to a temperature of 25° C. in a thermostat was placed in a 500-mL beaker, and 0.9±0.001 g of the water-absorbent resin was dispersed therein with stirring using a magnetic stirrer bar (8 mm in diameter×30 mm, without a ring) at 600 rpm, so as not to form unswollen lumps. The dispersion was allowed to stand with stirring for 60 minutes, such that the water-absorbent resin was sufficiently swollen.

Next, the mass (W0) of a cylinder with an inside diameter of 60 mm and a height of 70 mm, having a 400-mesh stainless steel mesh attached to the bottom, was measured. Then, all contents in the beaker were poured into the cylinder, and the water was drained for 1 minute through a wire gauze with a thickness of 1 mm and a mesh of 1.5 mm. The mass (W1) of the cylinder (containing the water absorbent resin after draining the water) after draining the water for 1 minute was measured. Then, a water-absorption factor of the water-absorbent resin after draining the water for 1 minute was calculated from W0 and W1, according to the following equation:

Water-absorption factor$(g/g)$ after draining the water for 1 minute=$\{[W1-(W0+\text{mass of the water-absorbent resin})]/\text{mass of the water-absorbent resin}\}\times 100$ Next, a weight capable of evenly applying a load of 21 g/cm² was placed on the water-absorbent resin after draining of the water, and the water was again drained for 15 minutes through the wire gauze. The mass (W2) of the cylinder (containing the water-absorbent resin after draining the water under pressure) after draining the water under pressure was measured. Then, a water-absorption factor of the water-absorbent resin after draining the water under pressure for 15 minutes was calculated from W2 and W0, according to the following equation:

Water-absorption factor$(g/g)$ after draining the water under pressure for 15 minutes=$\{[W2-(W0+\text{mass of the water-absorbent resin})]/\text{mass of the water-absorbent resin}\}\times 100$ From the water-absorption factor after draining the water for 1 minute and the water-absorption factor after draining the water under pressure for 15 minutes, the physiological saline-retention ratio under a load was calculated as follows:

Physiological saline-retention ratio under a load (%)=$\{$(water-absorption factor after draining the water under pressure for 15 minutes)/(water-absorption factor after draining the water for 1 minute)$\}\times 100$ <Amount of Re-Wet in Absorbent Article>

(1) Preparation of Artificial Urine 60 g of sodium chloride, 1.8 g of calcium chloride dihydrate, 3.6 g of magnesium chloride hexahydrate, and a suitable amount of distilled water were placed in a 10-L container, and completely dissolved. Next, 0.02 g of polyoxyethylene nonylphenyl ether was added, and then distilled water was added to adjust the mass of the entire aqueous solution to 6000 g. Lastly, the resulting product was colored with a small amount of Blue No. 1 to obtain artificial urine.

(2) Preparation of Water-Absorbent Sheet

A homogenous mixture of 30 parts by mass of an ethylene-vinyl acetate copolymer (EVA; melting point: 95° C.) as an adhesive and 90 parts by mass of the water-absorbent resin was charged into an inlet of a roller-type sprayer (SINTERACE M/C from Hashima Co., Ltd.). Separately, a polypropylene spunbond-melt blown-spunbond (SMS) with a width of 30 cm (a nonwoven fabric hydrophilized with a hydrophilizing agent (weight per unit area: 13 g/m², thickness: 150 μm, polypropylene content: 100%, hydrophilic degree: 16; referred to as "nonwoven fabric A")) was laid over a conveyor in the lower section of the sprayer. Next, the spraying roller and the conveyor in the lower section were operated to uniformly laminate the mixture onto the nonwoven fabric at a weight per unit area of 300 g/m².

The resulting laminate was sandwiched using another nonwoven fabric A, and then these parts were integrated by thermal fusion with a thermal laminator (linear adhesion press HP-600LF from Hashima Co., Ltd.) set at a heating temperature of 130° C. to obtain a water-absorbent sheet.

(3) Preparation of Absorbent Article

The obtained water-absorbent sheet was cut into a rectangular shape having a width of 30 cm and a length of 40 cm, and having a longitudinal direction corresponding to the warp direction (machine direction) of the nonwoven fabric. Next, a polyethylene-polypropylene air-through porous liquid-permeable sheet having the same size as that of the water-absorbent sheet and having a basis weight of 22 g/m² was positioned on an upper surface of the water-absorbent sheet, and a polyethylene liquid-impermeable sheet having the same size and the same basis weight was positioned on a lower surface of the water-absorbent sheet, such that the water-absorbent sheet was sandwiched between these sheets. As a result, an absorbent article was prepared.

(4) Measurement of Amount of Re-Wet in Absorbent Article

Next, the absorbent article was placed on a horizontal stage. A measurement device equipped with a cylinder having an inside diameter of 3 cm through which a liquid was to be added was placed on a central portion of the absorbent article. 50 mL of the artificial urine was added into the cylinder at a time, and the absorbent article was kept as is. At 30 and 60 minutes after the start of the first addition of the artificial urine, this procedure was performed on the same position as the first time. At 120 minutes after the start of the first addition of the test liquid, filter paper measuring 10 cm per side (54 pieces, having a total mass (Wd) of about 50 g), whose mass had been measured in advance, was placed near the position on the absorbent article to which the artificial urine was added, and a weight with a mass of 5 kg having a 10 cm×10 cm bottom surface was placed on the filter paper. After the load was applied for 5 minutes, the mass of the filter paper (We (g)) was measured, and the increased mass was determined as the amount of re-wet (g).

Production of Water-Absorbent Resin

Example 1

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 500 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the water bath was adjusted to 80° C., and the reaction mixture was heated for 60 minutes. As a result, first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.129 g (0.475 mmol) of 2,2'-azobis(2-amidinopropane) dihydrochloride as an azo-based compound and 0.0116 g (0.067 mmol) of ethylene glycol diglycidyl ether as an internal-crosslinking agent were added and dissolved. As a result, a second-stage aqueous monomer solution was prepared.

The rotation speed of the stirrer was changed to 1000 rpm, and then the atmosphere within the separable flask was cooled. The entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes. After the second-stage polymerization, the flask was immersed in an oil bath at 125° C. to heat the second-stage polymerization slurry to distill 239 g of water out of the system while refluxing n-heptane by azeotropic distillation of water and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 244.0 g of a water-absorbent resin with a median particle diameter of 400 μm in which spherical particles were aggregated.

Example 2

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 600 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the water bath was adjusted to 80° C., and the reaction mixture was heated for 60 minutes. As a result, first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.129 g (0.475 mmol) of 2,2'-azobis(2-amidinopropane) dihydrochloride as an azo-based compound and 0.0116 g (0.067 mmol) of ethylene glycol diglycidyl ether as an internal-crosslinking agent were added and dissolved. As a result, a second-stage aqueous monomer solution was prepared.

The rotation speed of the stirrer was changed to 1000 rpm, and then the atmosphere within the separable flask was cooled. The entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes. After the second-stage polymerization, the flask was immersed in an oil bath at 125° C. to heat the second-stage polymerization slurry to distill 244 g of water out of the system while refluxing n-heptane into the system by azeotropic distillation of water and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 243.0 g of a water-absorbent resin with a median particle diameter of 390 μm in which spherical particles were aggregated.

Comparative Example 1

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 600 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the rotation speed of the stirrer was changed to 1000 rpm, and the flask was heated in an oil bath at 125° C. to distill 23 g of water out of the system while refluxing n-heptane by azeotropic distillation of water and n-heptane. As a result, first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.11 g (0.00041 mol) of 2,2'-azobis(2-amidinopropane) dihydrochloride as an azo-based compound and 0.0116 g (0.000067 mol) of ethylene glycol diglycidyl ether as an internal-crosslinking agent were added and dissolved. As a result, a second-stage aqueous monomer solution was prepared.

The atmosphere within the separable flask was cooled. Then, the entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes.

After the second-stage polymerization, the flask was immersed in an oil bath at 125° C. to heat the second-stage polymerization slurry to distill 227 g of water out of the system while refluxing n-heptane into the system by azeotropic distillation of water and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 236.0 g of a water-absorbent resin with a median particle diameter of 380 μm in which spherical particles were aggregated.

Comparative Example 2

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 500 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the rotation speed of the stirrer was changed to 1000 rpm, and the flask was heated in an oil bath at 125° C. to distill 92 g of water out of the system while refluxing n-heptane into the system by azeotropic distillation of water and n-heptane. As a result, first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.11 g (0.00041 mol) of 2,2'-azobis(2-amidinopropane) dihydrochloride as an azo-based compound and 0.0116 g (0.000067 mol) of ethylene glycol diglycidyl ether as an internal-crosslinking agent were added and dissolved. As a result, a second-stage aqueous monomer solution was prepared.

The atmosphere within the separable flask was cooled. Then, the entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes.

After the second-stage polymerization, the flask was immersed in an oil bath at 125° C. to heat the second-stage polymerization slurry to distill 168 g of water out of the system while refluxing n-heptane into the system by azeotropic distillation of water and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 238.0 g of a water-absorbent resin with a median particle diameter of 370 μm in which spherical particles were aggregated.

Table 1 shows the results of evaluation of the water-absorbent resins produced in the examples and comparative examples as well as absorbent articles obtained with these water-absorbent resins, using the testing methods for evaluation described above.

TABLE 1

| | Cavity Area Ratio (%) | Physiological Saline-Retention Capacity (g/g) | Physiological Saline-Retention Ratio under a Load (%) | Amount of Re-Wet in Absorbent Article (g) |
|---|---|---|---|---|
| Example 1 | 3 | 42 | 76 | 0.8 |
| Example 2 | 6 | 45 | 77 | 0.6 |
| Comparative Example 1 | 11 | 40 | 69 | 3.7 |
| Comparative Example 2 | 11 | 46 | 71 | 3.3 |

As is clear from the results shown in Table 1, the water-absorbent resins of Examples 1 and 2 having a ratio of the area of cavity portions (cavity area ratio) of 10% or less as calculated according to Equation (1) above exhibited high physiological saline-retention ratios under a load, and effectively reduced the amount of re-wet when used in water-absorbent sheets. This shows that the water-absorbent resins of Examples 1 and 2 exhibit high liquid-retention capacities under a load and small amounts of re-wet even when they are used in an absorbent material having a low proportion of hydrophilic fibers.

REFERENCE SIGNS LIST

10 sample stage
11 water-absorbent resin
w particle length

The invention claimed is:

1. A water-absorbent resin comprising a polymer of a water-soluble ethylenically unsaturated monomer, wherein when a cross-sectional image of the water-absorbent resin is observed using X-ray computed tomography, the water-absorbent resin has a ratio of area of cavity portions (cavity area ratio) in the cross-sectional image of 10% or less, as calculated according to Equation (I):

cavity area ratio[%]={total cross-sectional area of cavity portions($B$) in the water-absorbent resin/(total cross-sectional area of resin portions($A$) in the water-absorbent resin+total cross-sectional area of cavity portions($B$) in the water-absorbent resin))×100     (I), wherein the water-absorbent resin has a substantially spherical shape or a shape in which particles having a substantially spherical shape are aggregated.

2. The water-absorbent resin according to claim 1, wherein the water-absorbent resin has a physiological saline-retention ratio under a load of 73% or more.

3. The water-absorbent resin according to claim 1, which is used in an absorbent material designed to have a ratio of hydrophilic fibers of 50% by mass or less in the absorbent material.

4. The water-absorbent resin according to claim 2, which is used in an absorbent material designed to have a ratio of hydrophilic fibers of 50% by mass or less in the absorbent material.

5. The water-absorbent resin according to claim 1, which is used in an absorbent material designed to have a ratio of hydrophilic fibers of 50% by mass or less in the absorbent material.

* * * * *